(12) United States Patent
Crisco

(10) Patent No.: US 10,960,188 B2
(45) Date of Patent: *Mar. 30, 2021

(54) DEVICES AND METHODS FOR MINIMALLY INVASIVE CORONARY BYPASS AND OTHER TREATMENTS

(71) Applicant: Access Flow Systems, LLC, Atlanta, GA (US)

(72) Inventor: L. Van Thomas Crisco, Jacksonville, FL (US)

(73) Assignee: ACCESS FLOW SYSTEMS, LLC, Atlanta, GA (US)

( * ) Notice: Subject to any disclaimer, the term of this patent is extended or adjusted under 35 U.S.C. 154(b) by 149 days.

This patent is subject to a terminal disclaimer.

(21) Appl. No.: 15/088,447

(22) Filed: Apr. 1, 2016

(65) Prior Publication Data

US 2016/0213899 A1 Jul. 28, 2016

Related U.S. Application Data

(60) Continuation of application No. 14/164,750, filed on Jan. 27, 2014, now Pat. No. 9,301,776, which is a (Continued)

(51) Int. Cl.
*A61M 27/00* (2006.01)
*A61B 17/34* (2006.01)
(Continued)

(52) U.S. Cl.
CPC ....... *A61M 27/002* (2013.01); *A61B 17/3421* (2013.01); *A61B 17/3468* (2013.01);
(Continued)

(58) Field of Classification Search
CPC .......... A61B 2017/00243; A61B 2017/00247; A61B 2018/00392; A61B 2017/306;
(Continued)

(56) References Cited

U.S. PATENT DOCUMENTS 5,071,407 A * 12/1991 Termin ................ A61F 2/88
604/104
5,380,316 A * 1/1995 Aita ................ A61B 18/245
606/15
(Continued)

FOREIGN PATENT DOCUMENTS

WO WO2008/005405 1/2008

OTHER PUBLICATIONS

Definition of Surround by Merriam-Webster.*
(Continued)

*Primary Examiner* — Jing Rui Ou
(74) *Attorney, Agent, or Firm* — Eversheds Sutherland (US) LLP

(57) ABSTRACT

Treatment methods and devices are provided for percutaneously accessing a patient's thoracic region via a controlled opening in the aorta, so that cardiac procedures, such as a coronary bypass procedure, can be performed in a minimally invasive manner. Advantageously, it may be possible to perform the procedure without placing the patient on cardiopulmonary bypass. The method may include percutaneously delivering at least one catheter into an aorta of a heart, forming a controlled opening in the aorta and pericardium via the at least one catheter to access a thoracic region within the patient's chest, and performing at least one coronary bypass graft procedure through the controlled opening.

18 Claims, 11 Drawing Sheets

Related U.S. Application Data division of application No. 12/329,052, filed on Dec. 5, 2008, now Pat. No. 8,663,321.

(60) Provisional application No. 60/992,860, filed on Dec. 6, 2007.

(51) Int. Cl.
*A61B 90/00* (2016.01)
*A61B 18/24* (2006.01)
*A61B 17/00* (2006.01)

(52) U.S. Cl.
CPC ..... *A61B 18/24* (2013.01); *A61B 2017/00243* (2013.01); *A61B 2090/3762* (2016.02); *A61B 2090/3966* (2016.02)

(58) Field of Classification Search
CPC ............ A61B 17/0057; A61B 17/3421; A61B 17/3468; A61B 18/24; A61B 2090/3762; A61B 2090/3966; A61M 27/002
See application file for complete search history.

(56) References Cited

U.S. PATENT DOCUMENTS

| | | | |
|---|---|---|---|
| 5,452,733 A | 9/1995 | Sterman et al. | |
| 5,716,340 A * | 2/1998 | Schweich, Jr. ... | A61M 25/1002 604/101.05 |
| 5,735,290 A | 4/1998 | Sterman et al. | |
| 5,785,704 A | 7/1998 | Bille et al. | |
| 5,799,661 A | 9/1998 | Boyd et al. | |
| 5,827,216 A | 10/1998 | Igo et al. | |
| 5,875,782 A | 3/1999 | Ferrari et al. | |
| 5,888,247 A | 3/1999 | Benetti | |
| 5,931,810 A | 8/1999 | Grabek | |
| 5,944,019 A | 8/1999 | Knudson et al. | |
| 5,972,013 A | 10/1999 | Schmidt | |
| 5,976,178 A * | 11/1999 | Goldsteen ............ | A61B 1/0058 128/898 |
| 6,092,526 A | 7/2000 | LaFontaine et al. | |
| 6,110,187 A | 8/2000 | Donlon | |
| 6,155,264 A * | 12/2000 | Ressemann .... | A61B 17/320758 128/898 |
| 6,156,009 A | 12/2000 | Grabek | |
| 6,162,195 A | 12/2000 | Igo et al. | |
| 6,206,004 B1 | 3/2001 | Schmidt et al. | |
| 6,226,542 B1 | 5/2001 | Reisfeld | |
| 6,325,067 B1 | 12/2001 | Sterman et al. | |
| 6,592,552 B1 | 7/2003 | Schmidt | |
| 6,613,062 B1 | 9/2003 | Leckrone et al. | |
| 6,666,844 B1 | 12/2003 | Igo et al. | |
| 6,711,436 B1 | 3/2004 | Duhaylongsod | |
| 6,837,848 B2 | 1/2005 | Bonner et al. | |
| 6,890,295 B2 | 5/2005 | Michels et al. | |
| 6,899,669 B2 | 5/2005 | Vito et al. | |
| 6,918,890 B2 | 7/2005 | Schmidt | |
| 6,918,908 B2 | 7/2005 | Bonner et al. | |
| 7,017,581 B2 | 3/2006 | Boyd et al. | |
| 7,018,402 B2 | 3/2006 | Vito et al. | |
| 7,028,692 B2 | 4/2006 | Sterman et al. | |
| 7,063,693 B2 | 6/2006 | Guenst | |
| 7,087,066 B2 | 8/2006 | Boldue et al. | |
| 7,131,447 B2 | 11/2006 | Sterman et al. | |
| 7,207,988 B2 | 4/2007 | Leckrone et al. | |
| 7,226,440 B2 | 6/2007 | Gelfand et al. | |
| 7,959,644 B2 | 6/2011 | Shriver | |
| 2001/0001812 A1 * | 5/2001 | Valley .............. | A61B 17/12022 604/96.01 |
| 2001/0003985 A1 * | 6/2001 | Lafontaine ................ | A61F 2/06 128/898 |
| 2002/0038120 A1 | 3/2002 | Duhaylongsod et al. | |
| 2004/0102732 A1 | 5/2004 | Naghavi et al. | |
| 2004/0116897 A1 | 6/2004 | Aboul-Hosn | |
| 2004/0116946 A1 * | 6/2004 | Goldsteen ............ | A61B 1/0058 606/153 |
| 2006/0079915 A1 | 4/2006 | Chin et al. | |
| 2006/0155366 A1 | 7/2006 | LaDuca et al. | |
| 2007/0021818 A1 | 1/2007 | De Gregorio | |
| 2007/0185566 A1 * | 8/2007 | Khitin ................ | A61B 17/0057 623/1.36 |
| 2007/0276433 A1 | 11/2007 | Huss | |
| 2008/0275542 A1 | 11/2008 | LaDuca et al. | |

OTHER PUBLICATIONS

Hansen Medical, "Discover Your Sixth Sense".
Levinson, M.M., "Learning Center: The Internal Mammary Artery," The Heart Surgery Forum.
Reifart, N., "Percutaneous In Situ Coronary Venous Arterialization: A Catheter-Based Procedure for Coronary Artery Bypass," J. Interven. Cardiol. 18: 491-495 (2005).
Archbold, R.A. et al., "Radial Artery Access for Coronary Angiography and Percutaneous Coronary Intervention," BMJ 329: 443-446 (2004).
Grech, E.D., "Percutaneous Coronary Intervention. I: History and Development," BMJ 326: 1080-1082 (2003).
Gunn, J. et al., "New Developments in Percutaneous Coronary Intervention," BMJ 327: 150-153 (2003).
American Heart Association, "Percutaneous Coronary Interventions (Previously Called Angioplasty, Percutaneous Transluminal Coronary [PTCA], or Balloon Angioplasty".
Torpy, J.M., "Percutaneous Coronary Intervention," JAMA 291: 778 (2004).
Mayo Clinic Staff, "Coronary Artery Disease Treatment: Angioplasty vs. Bypass," http://www.mayoclinic.com—AN01472 (Nov. 16, 2006).
Mayo Clinic Staff, "Coronary Angioplasty and Stenting: Opening Clogged Heart Arteries," http://www.mayoclinic.com—HQ00485 (Dec. 20, 2006).
Desterle, S.N. et al., "Percutaneous In Situ Coronary Venous Arterialization: Report of the First Human Catheter-Based Coronary Artery Bypass," Circulation 103: 2539-2543 (2001).
Rumsfeld, J.S. et al., "Health-Related Quality of Life After Percutaneous Coronary Intervention Versus Coronary Bypass Surgery in High-Risk Patients With Medically Refractory Ischemia," J. Am. Coll. Cardiol. 41: 1732-1738 (2003).
Cabrales, R., "Combination of Minimally Invasive Coronary Bypass and Percutaneous Coronary Intervention in Patients With Multivessel Disease," CTSNet (2004).
Rogers, J.H. et al., "Percutaneous Septal Sinus Shortening: A Novel Procedure for the Treatment of Functional Mitral Regurgitation," Circulation 113: 2329-2334 (2006).

* cited by examiner

DEVICES AND METHODS FOR MINIMALLY INVASIVE CORONARY BYPASS AND OTHER TREATMENTS

CROSS-REFERENCE TO RELATED APPLICATIONS

This is a continuation of U.S. application Ser. No. 14/164,750, filed Jan. 27, 2014, now U.S. Pat. No. 9,301,776, which is a divisional of U.S. application Ser. No. 12/329,052, filed Dec. 5, 2008, now U.S. Pat. No. 8,663,321, which claims the benefit of U.S. Provisional Application No. 60/992,860, filed Dec. 6, 2007. These applications are incorporated herein by reference in their entirety.

BACKGROUND OF THE INVENTION

The present invention relates generally to minimally invasive methods for performing cardiac medical and/or surgical procedures, and more particularly to percutaneous methods for performing a coronary artery bypass graft (CABG) procedure on a patient in need thereof.

Coronary artery disease remains a leading cause of morbidity and mortality in Western societies. A number of approaches have been developed for treating coronary artery disease. It is often sufficient to treat the symptoms with pharmaceuticals and lifestyle modification to lessen the underlying causes of the disease. In more severe cases, the coronary stenoses may be treated endovascularly using techniques such as balloon angioplasty, atherectomy, laser ablation, stenting, thrombectomy, and the like.

In still more severe cases where pharmaceutical treatment and/or conventional endovascular approaches have failed or are likely to fail, it may be necessary to perform a coronary artery bypass graft procedure using open surgical techniques. Such techniques require that a patient's sternum be opened, the chest spread apart to provide access to the heart, and the heart stopped. While very effective in many cases, the use of open surgery to perform coronary artery bypass grafting is highly traumatic to the patient. The procedure requires immediate postoperative care in an intensive care unit, hospitalization for five to ten days, and a recovery period as long as six to eight weeks.

Alternative techniques have been devised to perform coronary bypass surgical procedures thorascopically. Examples of such procedures are disclosed in U.S. Pat. Nos. 7,131,447 and 7,028,692 to Sterman et al., and in U.S. Pat. No. 5,888,247 to Benetii. Although such methods are believed to decrease morbidity, mortality, cost, and recovery time when compared to conventional open surgical coronary bypass procedures, they still require stopping the patient's heart and placing the patient on cardiopulmonary bypass.

It would be desirable to provide a better method for performing a coronary bypass procedure that is less invasive than open surgical or thoracoscopic techniques. It would also be desirable to provide an interventional procedure that does not require use of cardiopulmonary bypass.

SUMMARY OF THE INVENTION

Methods and devices are provided for performing a medical procedure on a patient's heart. In one aspect, the method includes (i) percutaneously delivering at least one catheter into an aorta of the heart; (ii) forming a hemostatic connection between the at least one catheter and an inner wall of the aorta; (iii) creating an aperture through the aorta and pericardium, said aperture being bounded by the hemostatic connection, thereby forming a controlled opening to access a thoracic region of the patient's chest through the at least one catheter; and (iv) performing a cardiac procedure through the controlled opening. In one embodiment, a method is provided for performing a coronary bypass procedure on a patient's heart comprising: (i) percutaneously inserting an end of at least one catheter into the ascending aorta; (ii) forming a controlled opening in a wall of the aorta via a lumen of the inserted end of the at least one catheter, wherein the controlled opening is outwardly directed from the wall of the aorta into a thoracic region within the patient's chest; and (iii) performing at least one coronary bypass graft procedure through the controlled opening.

DETAILED DESCRIPTION OF THE INVENTION

Figure 1:
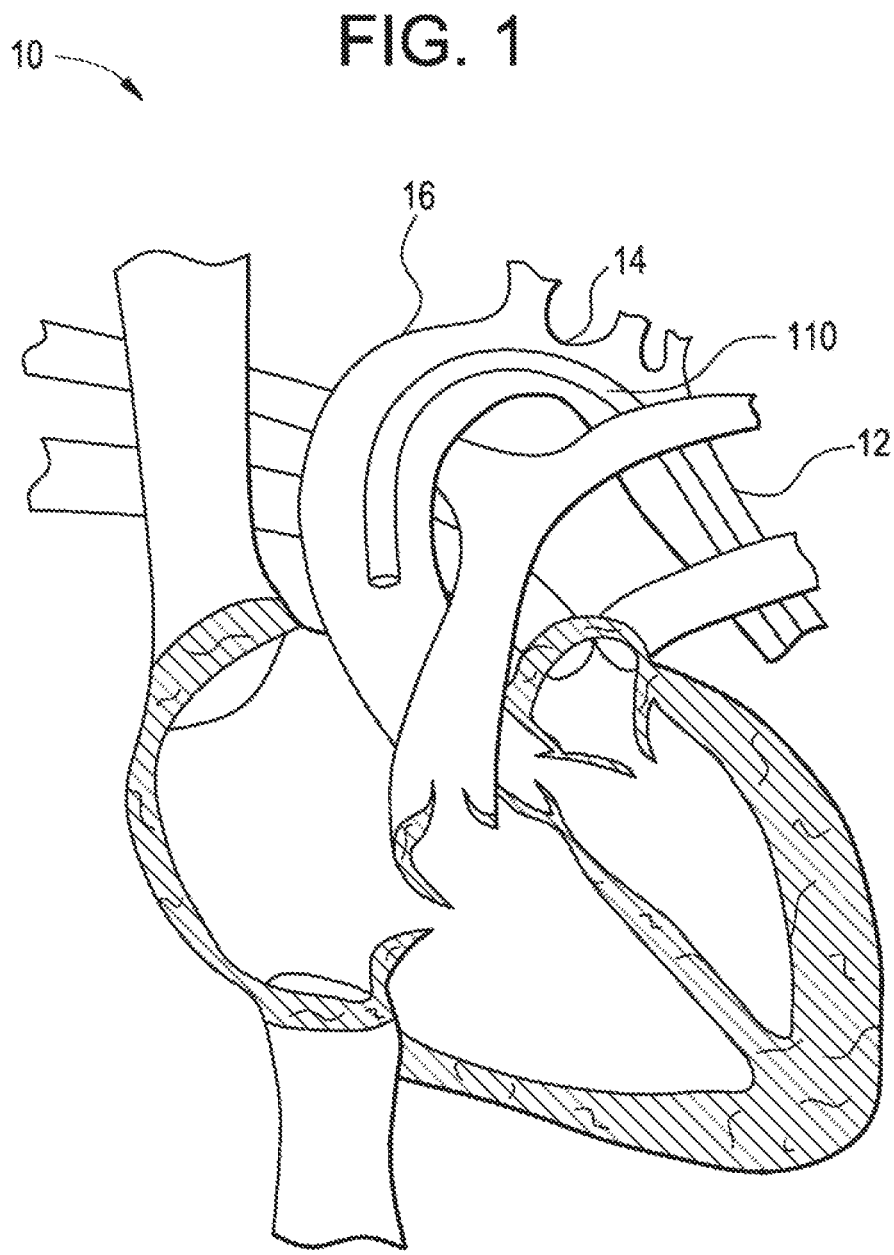
FIG. 1 illustrates a catheter disposed in a partial sectional view of a human heart and its associated proximate vascular system.

Methods and devices are provided for performing a variety of cardiac medical procedures on a patient in a minimally invasive manner. As used herein, the term "patient" refers primarily to a human adult or child, but also may include other suitable mammalian animals, for example in a pre-clinical trial or in veterinary care.

The interventional medical procedure preferably is conducted percutaneously, which involves accessing the heart via a blood vessel and a catheter introduced therein using a needle puncture. A wire may be introduced through the lumen of a needle and catheters can be delivered over the wire into the blood vessel and guided to the heart. In a preferred embodiment, the procedures may be conducted without placing the patient on cardiopulmonary bypass.

In one aspect, a method is provided for percutaneously performing a cardiac procedure on a patient's heart. In one embodiment, the method includes the steps of percutaneously delivering at least one catheter into the aorta above the beating heart; forming a hemostatic connection between the at least one catheter and an inner wall of the aorta or other vascular structure; creating an aperture through the ascending thoracic aorta or other vascular structure acting as an inflow conduit, said aperture being bounded by the hemostatic connection, thereby forming a controlled opening to access a thoracic region of the patient's chest through the at least one catheter; and performing a cardiac procedure through the controlled opening. In one embodiment, the cardiac procedure is a coronary bypass graft procedure. In other embodiments, the cardiac procedure may be a valve repair, a valve replacement, or a thermal and mechanical cardiac ablation procedure to correct arrhythmias. Other procedures known in the art may also be adapted to be performed through the controlled opening.

In a preferred embodiment, the procedure is conducted using computed tomography (CT) guidance. In another preferred embodiment, the at least one catheter comprises a Hansen Device™. These guidance tools are known in the art for use with conventional cardiac interventions.

In one embodiment, the coronary bypass graft procedure includes the steps of detaching a left internal mammary artery from a patient's inner thoracic wall; occluding blood flow in the left internal mammary artery; transecting a distal end of the left internal mammary artery; forming an anastomosis between the distal end of the left internal mammary artery and a coronary artery targeted for bypass; closing the controlled opening in the aorta and pericardium; and withdrawing the at least one catheter from the aorta.

The percutaneous coronary bypass graft procedure may be conducted as follows. The patient undergoing the procedure may be prepared in a conventional manner for cardiac catheterization with both groins prepared to permit access to the femoral arteries and veins and with the arms prepared to permit access to the radial or brachial arteries and veins. The patient may be sedated for the procedure using any appropriate means, including general anesthesia. Once anesthetized, the patient may be intubated with a double-lumen endobronchial tube, for example, which allows for the selective ventilation or deflation of the right and left lungs. The procedure generally should be conducted under systemic anticoagulation, such as with either heparin or bivalirudin, and in the presence of an effective antiplatelet therapy, such as aspirin and/or a thienopyrridine drug, like clopidogrel, or other antiplatelet agents.

After the patient has been prepared for the procedure, appropriate incisions are made and a catheter 110 is guided toward the heart 10 from the descending aorta 12 through the aortic arch 14 into the ascending aorta 16 (FIG. 1). The procedure generally may be conducted using fluoroscopic guidance or CT guidance to obtain the desired visualization. Other visualization techniques well known in the art, such as MRI, ultrasound, stereotaxis, also may be used.

Access from the left and right femoral arteries may be achieved in the usual fashion and a guide may be advanced to the ostium of the left coronary or the right coronary as is typically performed with angioplasty. Through this guide, a guidewire may be advanced across an anatomic stenosis in the right or left coronary system using conventional techniques. Another catheter 110 then may be advanced using the contralateral femoral access.

Figure 2:
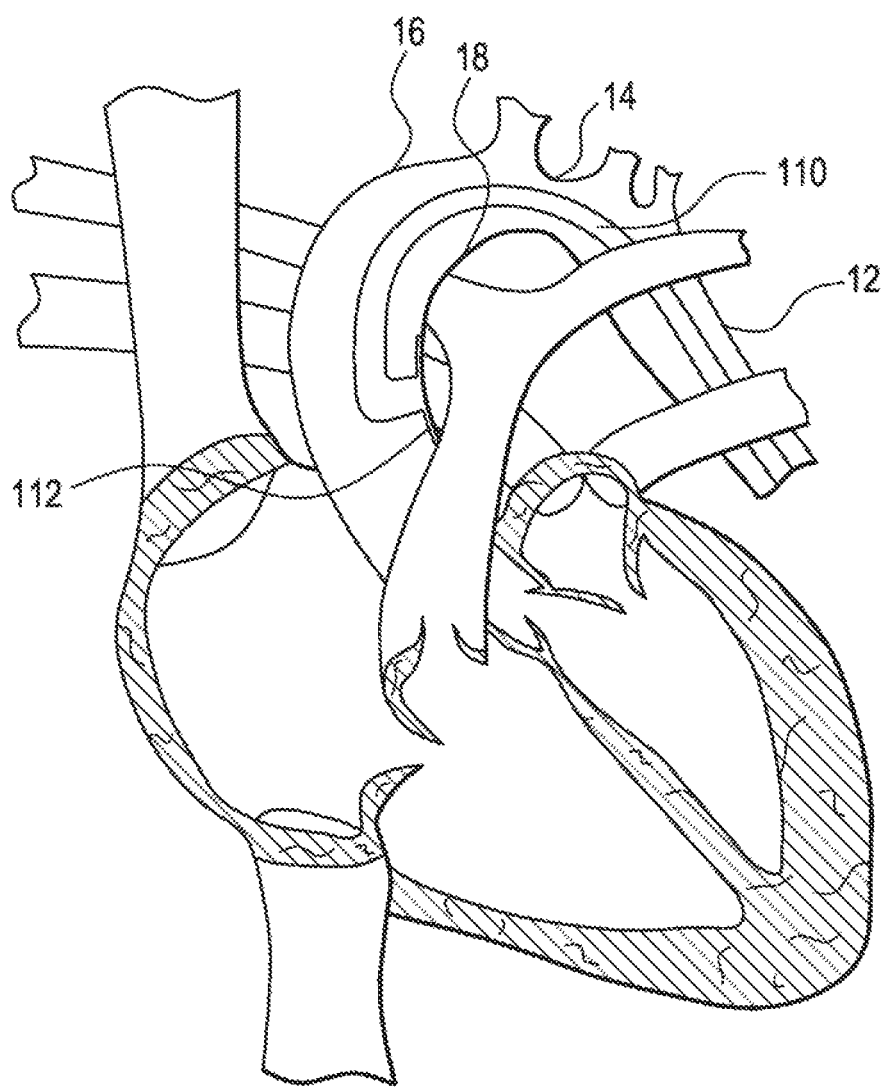
FIG. 2 illustrates a view of the heart of FIG. 1 with a hemostatic connection between the catheter and aorta according to one embodiment.
Figure 3A:
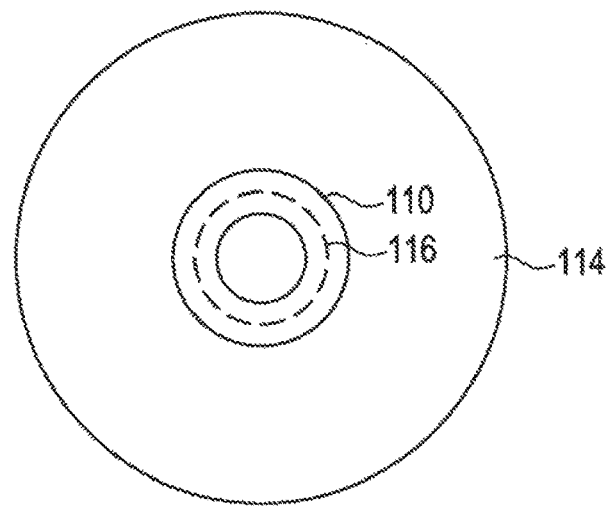
FIG. 3A illustrates a catheter according to one embodiment.
Figure 3B:
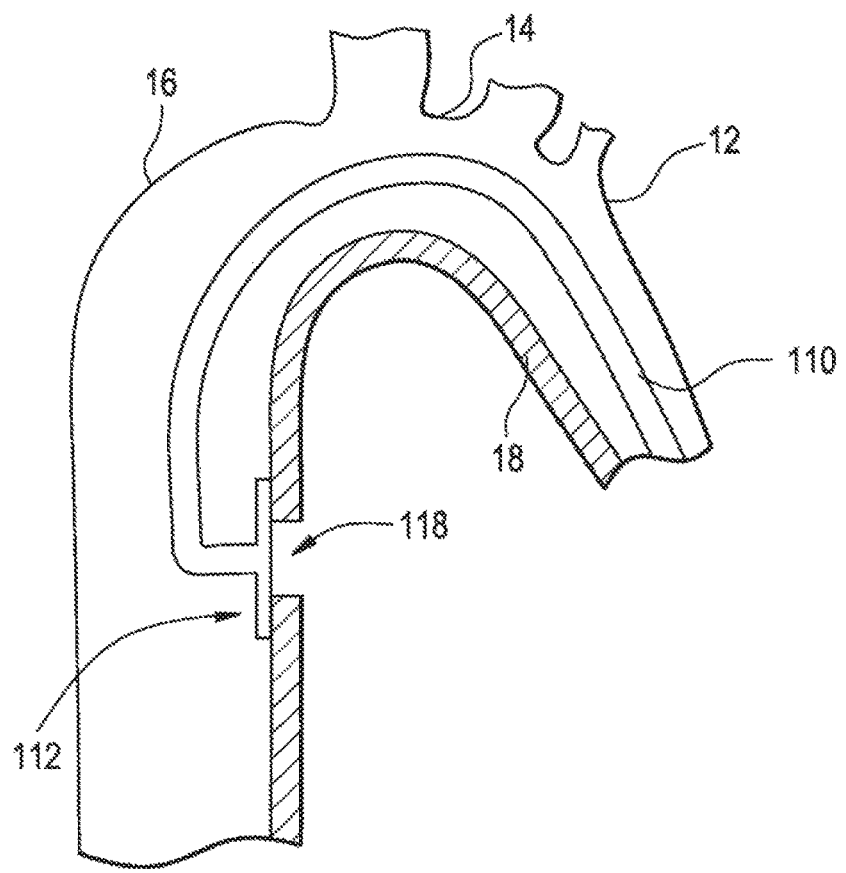
FIG. 3B illustrates a hemostatic connection and controlled opening in the aortic wall of the heart shown in FIG. 2.
Figure 4A:
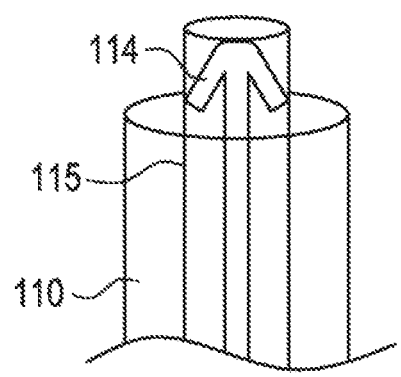
FIGS. 4A and 4B illustrate a flange in a non-expanded and expanded position in and extending from a catheter according to one embodiment.
Figure 4B:
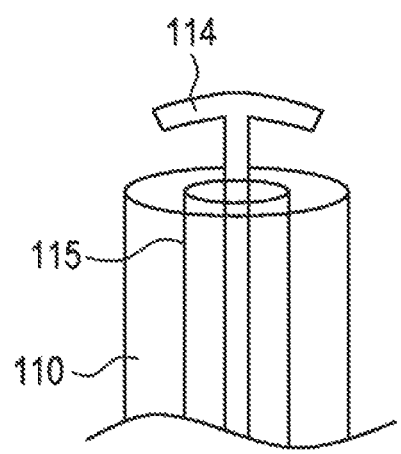

In one embodiment, the catheter 110 is used to form a hemostatic connection 112 with the inner aortic wall 18 in an anterolateral, or otherwise preferred, projection. Alternatively, the hemostatic connection may be made with the inner wall of any other suitable large vascular structure. The term "hemostatic connection" as used herein means a connection that substantially prevents the flow of blood or other fluids at the interface of the device and inner vascular wall (i.e., the lumen-aortic interface or catheter-aortic interface) (FIG. 2). In one embodiment, the catheter 110 includes a flange 114 that is part of the catheter itself (FIG. 3A). The flange 114 may expand upon removal of a sleeve 115 that keeps the flange in a non-expanded form until the distal end of the catheter 110 is in the desired position within the aorta, for example (FIGS. 4A and 4B). Those skilled in the art will appreciate that the flange may assume any suitable shape, non-limiting examples of which include a rectangular, circular, or elliptical form.

Figure 5:
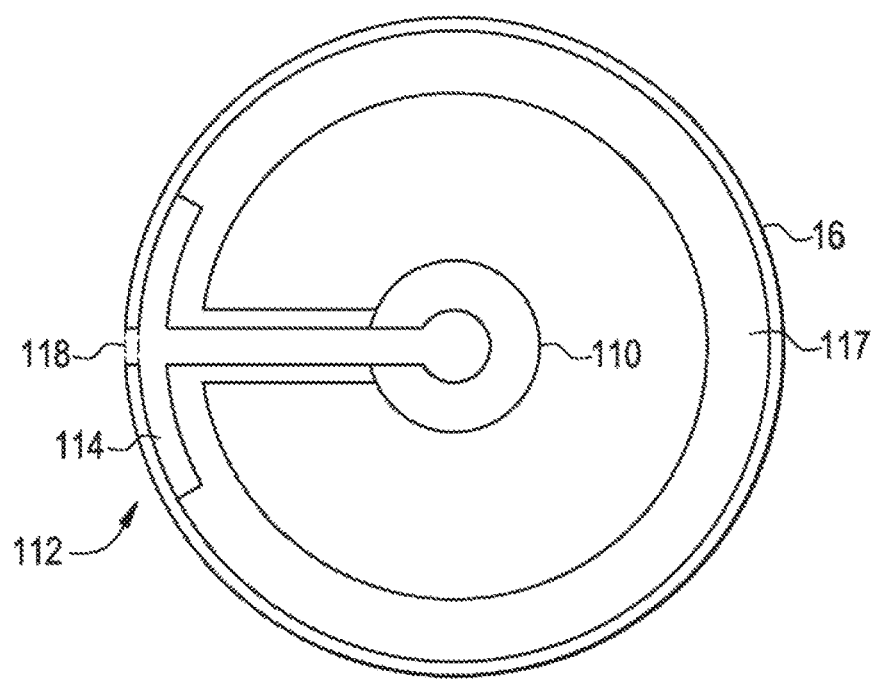
FIG. 5 illustrates a device and method for forming a hemostatic connection between the catheter and aorta according to one embodiment.
Figure 6:
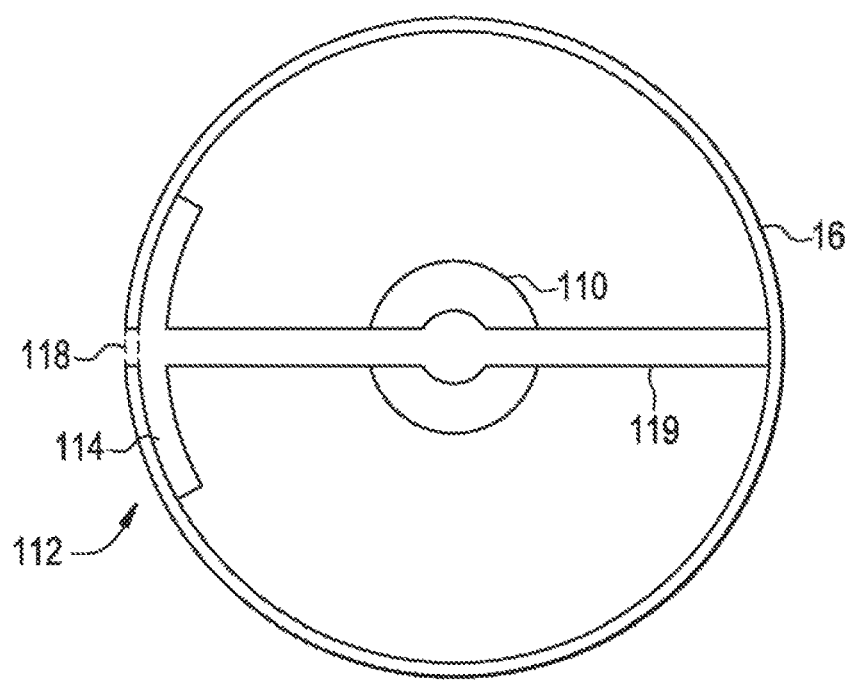
FIG. 6 illustrates a device and method for forming a hemostatic connection between the catheter and aorta according to another embodiment.

The hemostatic connection between the catheter and the inner aortic wall may be made using any suitable technique, including suction adherence, removable suture adherence, or magnetic pull from a source outside the body on the chest wall. For example, in one embodiment, the hemostatic connection 112 may be created by forming sutures 116 through the catheter wall 110 to the inner aortic wall 18, which may be tightened during the procedure as needed and removed after the procedure has been completed. The hemostatic connection 112 also may be created by inflating a non-occluding balloon 117 within the aorta 16 (FIG. 5). The non-occluding balloon should be inflated in such a way that it provides a sufficient amount of pressure against the flange 114, thereby forming a hemostatic connection between the flange and the inner aortic wall 18. Such non-occluding balloons are known to those in the art, non-limiting examples of which are disclosed in U.S. Patent Publication No. 2007/0021818 to De Gregorio and U.S. Patent Publication No. 2004/0102732 to Naghani et al. In one embodiment, the hemostatic connection 112 may be created by extending one or more counter-supports 119 within the aorta 16 opposite the flange 114 (FIG. 6). The one or more counter-supports should provide a sufficient amount of pressure to secure the flange 114 against the inner aortic wall 18 and form a hemostatic connection 112.

After the hemostatic connection 112 between the catheter 110 and inner aortic wall 18 has been established, a controlled wall opening 118 is created through the aortic wall into the thorax (not shown) using any suitable technique or device for forming the penetration. Non-limiting examples of such techniques may include use of a trocar through the catheter or use of a laser to create the controlled opening. In one embodiment, the aorto-thoracic controlled opening may be maintained by an anchoring device delivered through the catheter, such as a self-expanding or balloon expandable fixator. This anchoring device may remain or be removed upon aorto-coronary conduit placement. The controlled opening provides an access point for a joystick-driven blunt-tipped catheter, which may be manipulated under CT or MR guidance. Desirably, the catheter may be manipulated 360 degrees. Non-limiting examples of such catheters include the CT-guided Hansen Device™ (Hansen Medical, Mountain View, Calif.) or the MR-guided Stereotaxis Magnetic Navigation System™ (Stereotaxis Inc., St. Louis, Mo.).

With the left lung selectively deflated, the joystick driven catheter then may be used to dissect within the thorax to the pericardium. Once the pericardium may be visualized directly, access to the pericardium may be achieved using a mechanical puncture or laser opening. A guidewire may then be passed into the pericardium, thereby allowing a balloon occluding device to be advanced over the guidewire such that either side of the balloon would allow the center of the balloon (e.g., a dogbone shape) to forcibly tamponade the hole in the pericardium. After removing the wire, the pericardium then may be insufflated with carbon dioxide via the balloon to provide space in which to work in the pericardium. Alternatively, the pericardium may be simply incised and opened for direct access to the cardiac anatomy.

Figure 7:
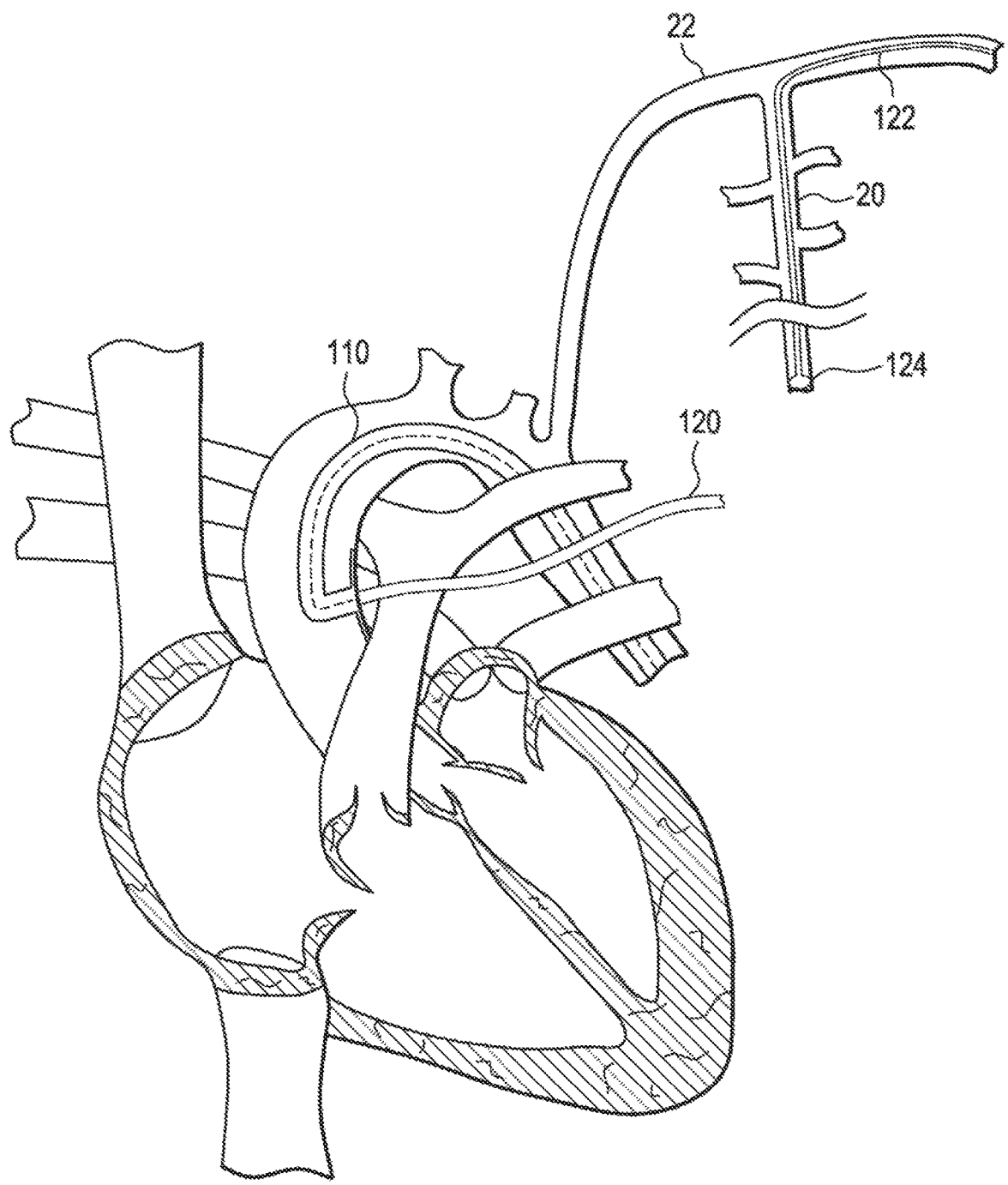
FIG. 7 illustrates a view of the heart of FIG. 1 undergoing a coronary bypass graft procedure according to one embodiment.

Once access to the thorax has been accomplished with the left lung selectively deflated, the left internal mammary artery 20 may be taken down from the patient's inner thoracic wall percutaneously by a Hansen Device™ or other suitable device 120 which is advanced through the catheter 110 (FIG. 7). Those skilled in the art will appreciate that access and manipulation of the left internal mammary artery may be achieved from a variety of different positions, non-limiting examples of such positions include the radial, brachial, or axillary positions, depending upon the selected access sheath and device size. In one embodiment, the left internal mammary artery is accessed by first selectively deflating the left lung through the endotracheal tube and maintaining ventilatory support through the right lung. The blood flow in the internal mammary artery 20 typically is stopped before take-down of the artery by introducing a separate catheter 122 through the left radial artery and subclavian artery 22 into the internal mammary artery and inflating a balloon 124 at the distal tip of the artery to occlude blood flow. In another embodiment, the blood flow in the left internal mammary artery is stopped using a proximal flow-occluding device. After occlusion of the blood flow within the left internal mammary artery 20, a laser tipped catheter 120 may be advanced through the aorto-thoracic catheter 110 via the controlled opening 118, and used to cut and seal the side branches of the left internal mammary artery 20, to dissect the left internal mammary artery from the thoracic wall, and to transect the distal tip of the artery. This process may involve simultaneous manipulation of the left radial-to-left internal mammary artery catheter 122, and the aorto-thoracic catheter 110 together to avoid trauma to the left internal mammary artery 20 as it is being taken down from the inner thoracic wall. Suitable laser tipped catheters are known in the art, or may fashioned to achieve this end (e.g., holmium lasers). Other commonly used interventional cardiology or surgical devices may also be employed to this end.

Figure 8:
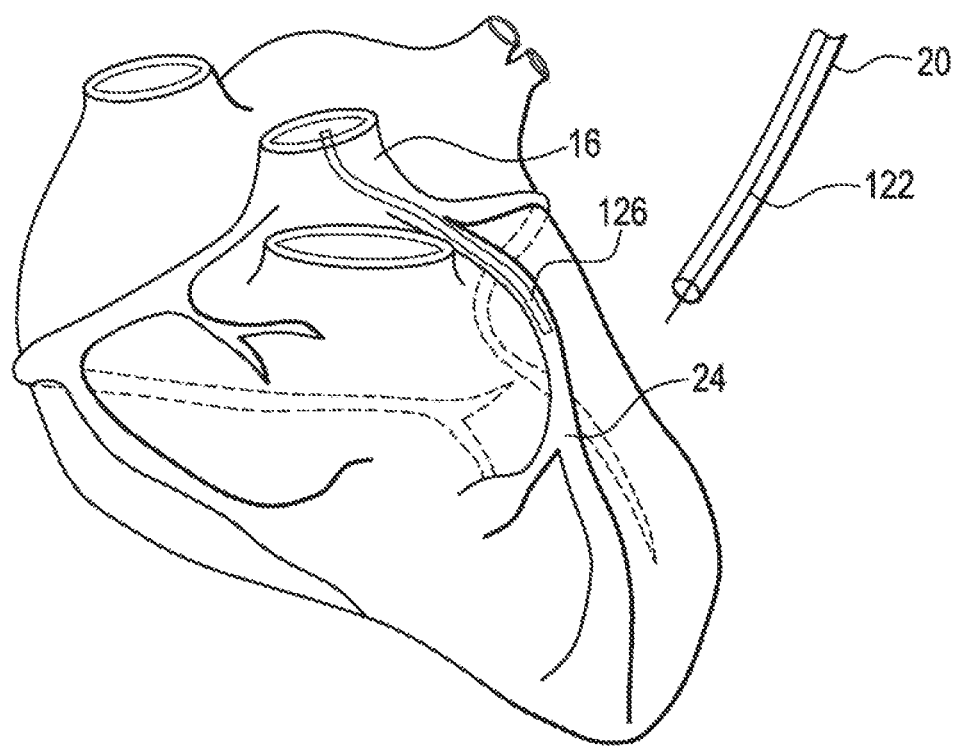
FIG. 8 illustrates a view of the heart of FIG. 5 undergoing a coronary bypass graft procedure according to one embodiment.

After harvesting and preparing the left internal mammary artery 20 for anastomosis, the target site of the coronary artery to be bypassed is identified. Typically, the diseased coronary artery which is the subject of the bypass is the left anterior descending (LAD) artery 24 (FIG. 8); however, the methods provided herein also are suitable for bypassing other arteries, including the right coronary artery, the obtuse marginal artery, the ramus intermedius artery, and the posterior descending artery.

After the take-down and transection of the left internal mammary artery 20, the left internal mammary artery may be manipulated and repositioned toward the opening of the pericardium (not shown) toward the surface of the LAD 24 on the top of the heart (not shown). In one embodiment, a pair of magnetic tipped catheters is used to align the left internal mammary artery and LAD. A non-limiting example of such a catheter is the MagneCath™ (Ample Medical, Foster City, Calif.). In one embodiment, a first MagneCath™ 126 is disposed in the LAD 24 (the endovascular MagneCath™) and a second MagneCath™ 122 is disposed in the left internal mammary artery 20 (the epivascular MagneCath™). The first and second MagneCath™ then are used to align the left internal mammary artery and LAD (FIGS. 9A and 9B).

Figure 10A:
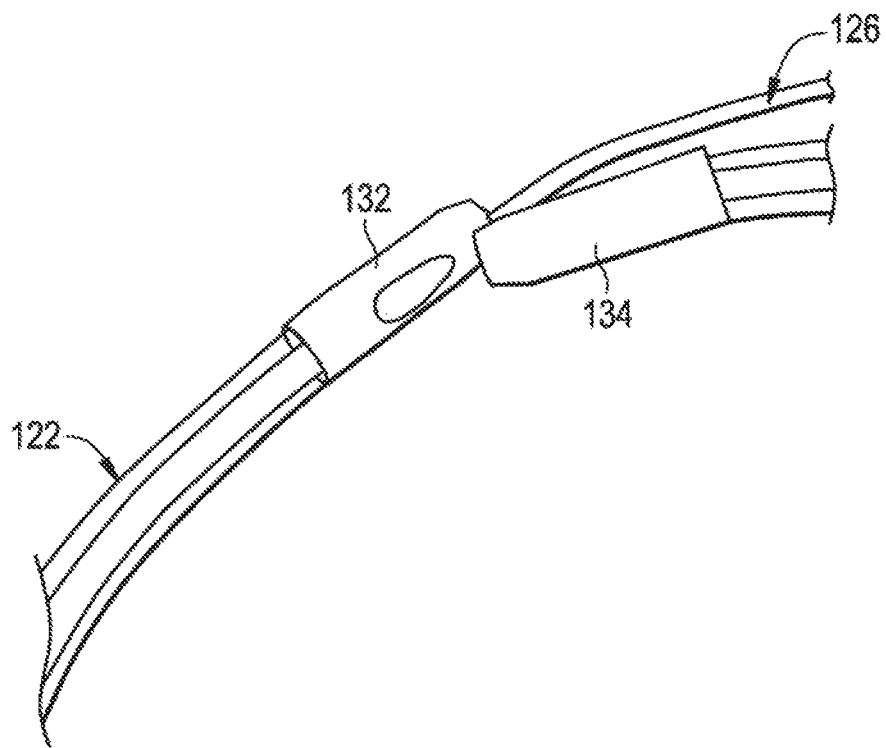
FIGS. 10A and 10B illustrate a magnetically linked catheter both before and after passage of a loop glide wire from a first catheter to a second catheter.
Figure 10B:
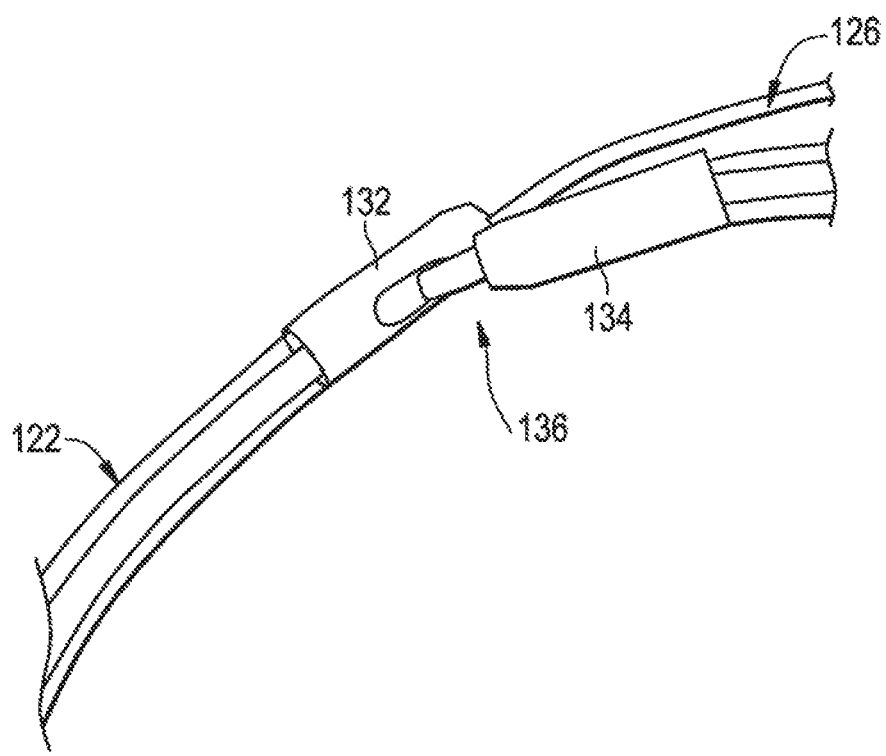

The MagneCath™ provides two complimentary shaped permanent magnets 132,134 on the distal tip of the catheter 122,126 which link together (FIGS. 10A and 10B, illustrated in Circulation 113:2329-34, 2330 (2006)). Such a device allows an exact linkage between the first MagneCath™ in the LAD distal to the significant coronary lesion and the second MagneCath™ in the left internal mammary artery at the epicardial coronary distal to the lesion. The MagneCath™ 126 is a hypotube with a guidewire lumen 136 and magnet 134 at the distal tip that complimentarily attaches to the interlocking magnet 132 of a second MagneCath™ 122. The attachment of the two MagneCath™ allows for the forceable puncturing from one hypotube through the MagneCath™ 126 into the second MagneCath™ 122. Once passed through the complimentary MagneCath™, the guidewire 136 acts as a tether over which one can deliver devices, balloons, or in this case attach one vascular structure to another.

The MagneCath™ tips on either side of the selected artery wall of interest (for example, the left internal mammary artery or LAD) may be manipulated such that they link magnetically. After the catheters are mated, a crossing guidewire 136 may be advanced from the endovascular MagneCath™ 126 into the epivascular MagneCath™ 122, linking the two devices. This guidewire 136 may then be passed from the artery into the aorto-thoracic catheter 110 and externalized as a continuous right common femoral artery-to-left common femoral artery loop or right common femoral artery-to-left radial artery loop to remove the MagneCath™. Over this guidewire, a proximal occlusion balloon may be used to interrupt blood flow within the selected coronary artery, while manipulation in the epicardial space is performed.

Figure 9A:
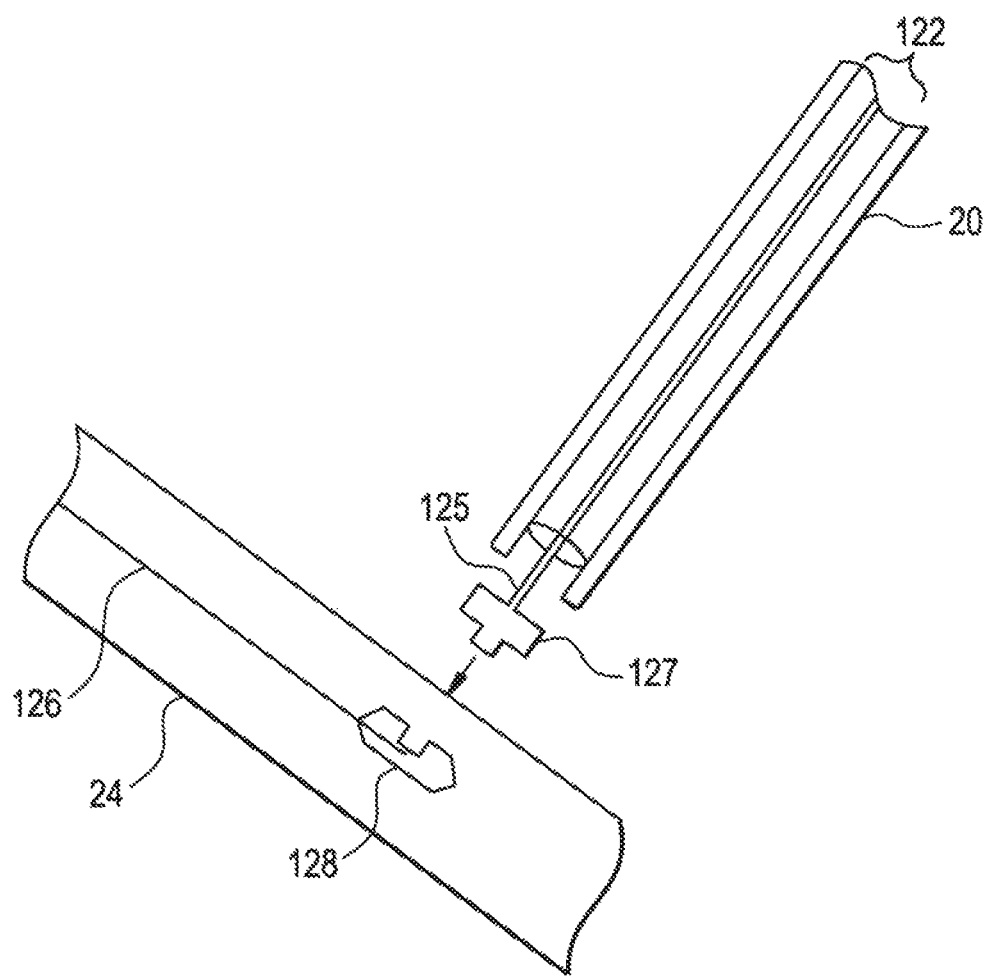
FIGS. 9A and 9B illustrate a lock and key stent for use in a coronary bypass graft procedure before and after, respectively according to one embodiment.
Figure 9B:
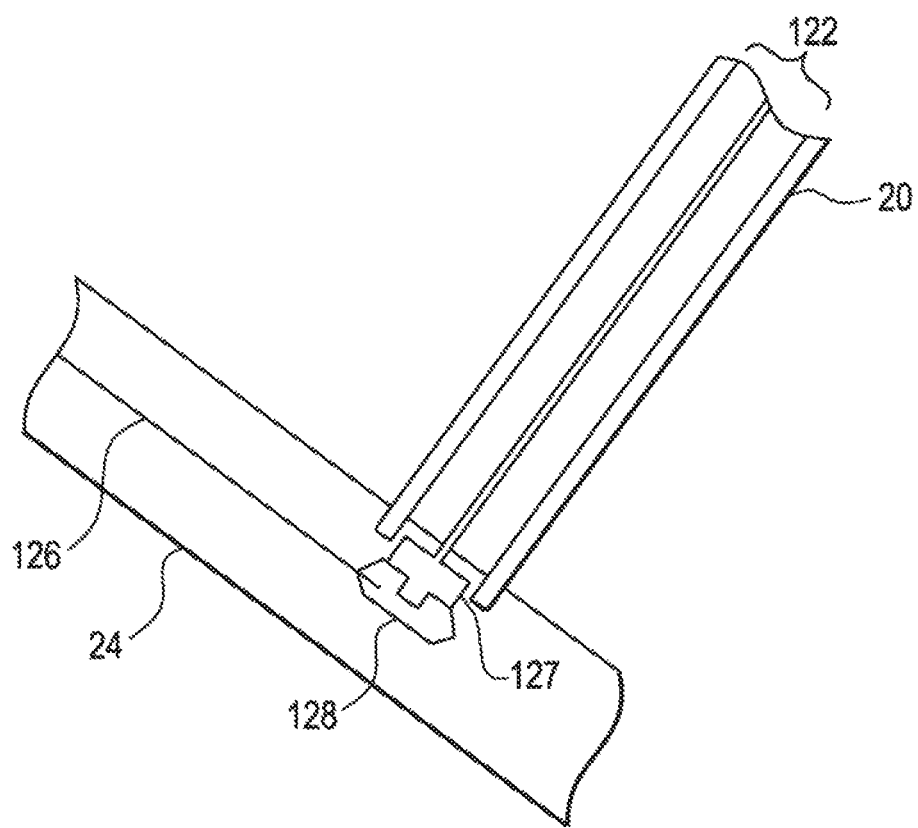
Figure 11:
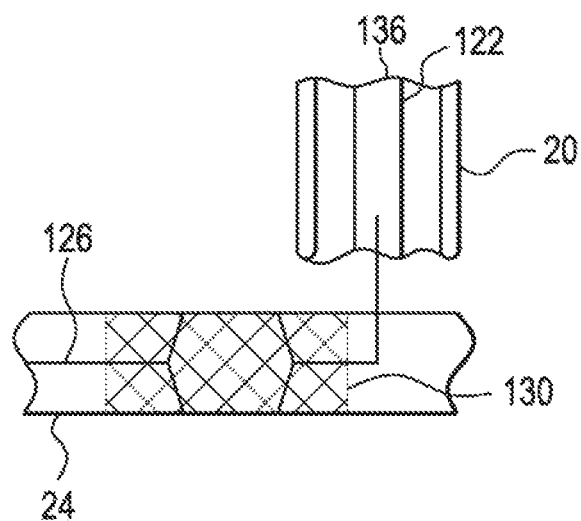
FIG. 11 illustrates a stent for the formation of an end-to-side anastomosis in a coronary bypass graft procedure according to one embodiment.

In one embodiment, a locking vascular connector is implanted on the distal tip of the left internal mammary artery 20 via a thoracotomy in the anterior chest wall after the take-down of the left internal mammary artery 20 and before the movement of the left internal mammary artery into position (FIGS. 9A and 9B). Alternatively, a stent 130 may be placed in the LAD 24 to allow for use of an occlusion balloon catheter in the LAD, thereby accommodating use of an end-to-side anatastomosis between the left internal mammary artery and LAD (FIG. 11).

In one embodiment, the tip of the left internal mammary artery is affixed to the LAD with a stent-like self-expanding nitinol vascular connector, which allows for anastomosis to the coronary. The vascular connector may comprise a singular device or multiple separate but complimentary or cooperative devices 127, 128 (e.g., a lock and key) disposed in the left internal mammary artery 20 and in the LAD 24 (FIGS. 9A and 9B). The vascular connector 127 may be applied to the tip of the left internal mammary artery 20 using direct force applied from the lumen outwardly or by suture to the left internal mammary artery through the patient's chest using a thoracotomy or through the aortothoracic catheter or the radial catheter, while the vascular connector 128 may be attached to the LAD using direct expansive force. In a particular embodiment, the vascular connector 128 may be deployed by removal of a sheath closure mechanism, similar to currently known or commercially available self-expanding stents. The vascular connector may further comprise a drug coating, similar to currently available drug eluting stents.

Other techniques known to those skilled in the art for joining the internal mammary artery and the LAD include suturing, laser welding, microstapling, using a bioadhesive (e.g., BioGlue™) or a combination thereof.

Following completion of the coronary anastomosis, the balloon occluding catheter of the left internal mammary artery may be deflated and removed, allowing blood to flow through the left internal mammary artery into the LAD. The catheter and Hansen Device™ is withdrawn from the thorax back through the catheter lumen-aortic interface, the aortic wall closed (sealed), and the catheters withdrawn. The groin and radial penetrations finally may be repaired as necessary.

It also is contemplated herein that a similar approach may be taken with the right internal mammary artery or using harvested saphenous veins. For example, in an alternative embodiment, a saphenous vein may be harvested from any suitable location. In one alternative embodiment, an arterial graft is harvested from the gastroepipolic artery, the gastric artery, the radial artery, the femoral artery, the splenic artery, or the like. Two vascular connectors may be applied to each end of the vein or arterial conduit to allow the vein or artery to be pulled forcibly or advanced using the MagneCath™-delivered guidewire. A flexible-tipped guidewire may be passed through the coronary catheter down the vessel, out the coronary artery through the MagneCath™ into the lumen of the pericardial balloon, and then out the catheter through the aorta to the femoral artery. The vein then may be advanced over the guidewire through the aortothoracic catheter into the thorax, down the wire through the pericardium, and attached to the coronary artery. A coronary arteriotomy may be necessary to advance a vein with a vascular connector over the tip. Once anastomosed to the coronary at the distal tip of the vein, the proximal aspect of the vein may be anastomosed to the thoracic aorta. A self-expanding nitinol vascular connector at either end of the vein optionally may be expanded. Such a procedure would provide an alternative method for coronary revascularization, providing a conduit for flow from the thoracic aorta down to the coronary artery.

Thus, the procedures described herein provide an approach for utilizing percutaneous and aorto-thoracic means of facilitating anastomosis of bypass conduits, the left or right internal mammary artery, or saphenous vein bypass grafts, achieving procedures which otherwise would require open chest coronary artery bypass grafting around significant stenoses in the native coronary anatomy. It is believed that such procedures may result in decreased morbidity, mortality, cost, and recovery time when compared to conventional surgical coronary bypass procedures.

Publications cited herein and the materials for which they are cited are specifically incorporated herein by reference. Modifications and variations of the methods and devices described herein will be obvious to those skilled in the art from the foregoing detailed description. Such modifications and variations are intended to come within the scope of the appended claims.

I claim:

1. A system for performing a percutaneous vascular or cardiac procedure, the system comprising:
   a percutaneous catheter having a distal end for insertion into a vein or artery of a patient;
   a sealing portion at the distal end which is configured to releasably form a hemostatic connection between the catheter and an inner wall of the vein or artery to form an interface between the sealing portion and the inner wall of the vein or artery, wherein the sealing portion is configured to form the hemostatic connection around a portion of the inner wall of the vein or artery, the hemostatic connection substantially preventing blood from flowing through the interface;
   a balloon configured to releasably secure the sealing portion against the inner wall to form the hemostatic connection, wherein the balloon surrounds the catheter; and
   a penetration device configured to pass through the catheter and form an aperture through the vein or artery while maintaining the hemostatic connection between the catheter and the inner wall, the aperture being bounded by the hemostatic connection.

2. The system of claim 1, wherein the sealing portion comprises a flange that is part of the catheter.

3. The system of claim 2, wherein the flange has an elliptical form.

4. The system of claim 1, wherein the penetration device comprises a laser.

5. The system of claim 1, wherein the penetration device comprises a trocar or other mechanical puncture.

6. A method for performing a percutaneous vascular or cardiac procedure comprising:
   providing the system of claim 1;
   inserting the distal end of the percutaneous catheter into a vein or an artery of a patient;
   placing the sealing portion against an inner wall of the vein or artery to form an interface between the sealing portion and the inner wall of the vein or artery;
   forming, with aid of the balloon, a hemostatic connection between the catheter and the inner wall of the vein or artery; and then
   forming, with the penetration device, an aperture through the vein or artery while the hemostatic connection is maintained between the catheter and the inner wall, wherein the aperture is bounded by the hemostatic connection.

7. The method of claim 6, further comprising performing a procedure using access through the aperture.

8. The method of claim 7, wherein the procedure using access through the aperture comprises a coronary bypass procedure.

9. The system of claim 1, wherein the balloon has an annular shape.

10. The system of claim 1, wherein the balloon is a non-occluding balloon.

11. The system of claim 1, wherein the balloon defines a passageway when the balloon is in an inflated state, and wherein the passageway is configured to allow blood to flow therethrough.

12. The system of claim 11, wherein the passageway is defined between the balloon and the catheter.

13. The system of claim 1, wherein the balloon is configured to press the sealing portion against the inner wall to form the hemostatic connection when the balloon is in an inflated state.

14. The system of claim 1, wherein the balloon is configured to engage a portion of the inner wall opposite the sealing portion when the balloon is in the inflated state.

15. A method for performing a medical procedure on a patient's heart comprising:
   percutaneously delivering a distal end of at least one catheter into an aorta of the patient's heart, wherein the distal end of the at least one catheter comprises a sealing portion, and wherein a balloon surrounds the at least one catheter and is configured to releasably secure the sealing portion against an inner wall of the aorta;
   releasably forming, with the aid of the balloon, a hemostatic connection between the at least one catheter and the inner wall to form an interface between the sealing portion and the inner wall; and then creating an aperture through the aorta and pericardium while maintaining the hemostatic connection between the at least one catheter and the inner wall, the aperture being bounded by the hemostatic connection, thereby forming a controlled opening to access a thoracic region of the patient's chest through the at least one catheter; and performing a cardiac procedure through the controlled opening.

16. The method of claim 15, wherein releasably forming the hemostatic connection between the catheter and the inner wall comprises inflating the balloon.

17. The method of claim 15, further comprising allowing blood to flow through a passageway defined by the balloon when the balloon is in an inflated state.

18. The method of claim 17, wherein the passageway is defined between the balloon and the catheter.

* * * * *